(12) United States Patent
Vilasi et al.

(10) Patent No.: US 9,107,577 B2
(45) Date of Patent: Aug. 18, 2015

(54) EXPANDABLE INTER VIVOS TUBE AND METHOD OF MANUFACTURING SAME

(71) Applicants: Joseph A. Vilasi, Lakewood Ranch, FL (US); Joseph D'Ambrosio, Ridgefield, CT (US)

(72) Inventors: Joseph A. Vilasi, Lakewood Ranch, FL (US); Joseph D'Ambrosio, Ridgefield, CT (US)

( * ) Notice: Subject to any disclaimer, the term of this patent is extended or adjusted under 35 U.S.C. 154(b) by 0 days.

(21) Appl. No.: 14/446,457

(22) Filed: Jul. 30, 2014

(65) Prior Publication Data

US 2015/0011828 A1 Jan. 8, 2015

Related U.S. Application Data

(63) Continuation-in-part of application No. 14/231,541, filed on Mar. 31, 2014, which is a continuation of application No. 13/662,552, filed on Oct. 29, 2012, now abandoned, and a continuation-in-part of application No. 14/300,324, filed on Jun. 10, 2014, which is a continuation-in-part of application No. 13/662,552, filed on Oct. 29, 2012, now abandoned, and a continuation-in-part of application No. 14/109,880, filed on Dec. 17, 2013, which is a continuation-in-part of application No. 13/662,553, filed on Oct. 29, 2012.

(60) Provisional application No. 61/911,589, filed on Dec. 4, 2013, provisional application No. 62/023,908, filed on Jul. 13, 2014.

(51) Int. Cl.
*A61B 1/00* (2006.01)
*A61M 16/04* (2006.01)
*A61M 25/10* (2013.01)
*A61M 16/08* (2006.01)
*A61M 16/20* (2006.01)

(52) U.S. Cl.
CPC .......... *A61B 1/00165* (2013.01); *A61B 1/00082* (2013.01); *A61M 16/044* (2013.01); *A61M 16/0418* (2014.02); *A61M 16/0438* (2014.02); *A61M 16/0477* (2014.02); *A61M 16/0816* (2013.01); *A61M 25/1025* (2013.01); *A61M 16/0434* (2013.01); *A61M 16/0445* (2014.02); *A61M 16/0454* (2014.02); *A61M 16/0465* (2013.01); *A61M 16/0497* (2013.01); *A61M 16/0833* (2014.02); *A61M 16/208* (2013.01); *A61M 2205/0216* (2013.01); *A61M 2210/1028* (2013.01)

(58) Field of Classification Search
CPC .......... A61B 1/00165; A61B 1/00082; A61M 16/044; A61M 16/0438; A61M 16/0816; A61M 16/0418; A61M 16/0477; A61M 16/0454; A61M 16/0833; A61M 16/208; A61M 16/0434; A61M 16/0465; A61M 16/0497; A61M 16/0445; A61M 25/1025; A61M 2210/1028; A61M 2205/0216
See application file for complete search history.

(56) References Cited

U.S. PATENT DOCUMENTS 4,722,335 A * 2/1988 Vilasi ..................... 128/207.14
5,647,358 A 7/1997 Vilasi (Continued)

*Primary Examiner* — Justine Yu
*Assistant Examiner* — Timothy Stanis
(74) *Attorney, Agent, or Firm* — Law Office of Carl Giordano, PC

(57) ABSTRACT

A flexible expandable inter vivos tube includes at least one arched segmented portion, a corresponding movable element and at least one positioning mechanism. The at least one arched segmented portion and corresponding movable element forming a flexible closed longitudinally expandable tube. The at least one arched segment includes an H-shaped connector having at least one cavity that allows variable slidable movement of a free end portion of the corresponding movable element. A balloon is contained in each of the at least one cavity so that the hydraulic or air pressure within balloon expands the movable element and, thus, the circumference of the flexible inter vivos tube is increased.

20 Claims, 15 Drawing Sheets

(56) References Cited

U.S. PATENT DOCUMENTS

| | | |
|---|---|---|
| 6,027,508 A * | 2/2000 | Ren et al. .................. 606/108 |
| 6,408,850 B1 | 6/2002 | Sudge |
| 2005/0224079 A1 * | 10/2005 | Green .................. 128/207.14 |
| 2008/0078399 A1 * | 4/2008 | O'Neil et al. ............ 128/207.14 |
| 2008/0115789 A1 | 5/2008 | Green |
| 2010/0313894 A1 | 12/2010 | Crumback |
| 2012/0109179 A1 * | 5/2012 | Murphy et al. ............... 606/194 |

* cited by examiner

EXPANDABLE INTER VIVOS TUBE AND METHOD OF MANUFACTURING SAME

CLAIM OF PRIORITY

This application
claims,
  pursuant to 35 USC 119, the benefit of the earlier filing
    date of, and priority to, that application entitled
    "Expandable Inter Vivos Tube and Method of Manufacturing Same," filed on Jul. 13, 2014 and afforded
    Ser. No. 62/023,908 (JVilasi-005P),
and further claims
  pursuant to 35 USC 120, as a continuation-in-part, the
    benefit of the earlier filing date of, and priority to, that
    application entitled;
    "Expandable Inter Vivos Tube," filed on Mar. 31, 2014
      and afforded Ser. No. 14/231,541 (JVilasi-001CON-1), which claimed,
  pursuant to 35 USC 120, as a continuation, the benefit of
    the earlier filing data of, and priority to that patent
    application entitled;
    "Expandable Inter Vivos Tube," filed on Oct. 29, 2012
      and afforded Ser. No. 13/662,552 (JVilasi-001)
      (abandoned),
and further claims,
  pursuant to 35 USC 120, as a continuation-in-part, the
    benefit of the earlier filing date of, and priority to that
    patent application entitled:
    "Expandable Inter Vivos Tube," filed on Jun. 10, 2014
      and afforded Ser. No. 14/300,324 (JVilasi-004),
      which claimed
  pursuant to 35 USC 120, as a continuation in part, the
    benefit of the earlier filing data of and priority to that
    patent application entitled;
    "Expandable Inter Vivos Tube," filed on Oct. 29, 2012
      and afforded Ser. No. 13/662,552 (JVilasi-001)
      (abandoned),
and further claims
  pursuant to 35 USC 120, as a continuation-in-part, the
    benefit of the earlier filing data of, and priority to, that
    patent application entitled:
    "Expandable Inter Vivos Tube," filed on Mar. 28, 2014
      and afforded Ser. No. 14/228,891 (JVilasi-003),
      which claimed,
  pursuant to 35 USC 120, as a continuation-in-part, the
    benefit of the earlier filing data of and priority to that
    patent application entitled;
    "Expandable Inter Vivos Tube," filed on Oct. 29, 2012
      and afforded Ser. No. 13/662,552 (JVilasi-001)
      (abandoned),
and further claims
  pursuant to 35 USC 120, as a continuation-in-part, the
    benefit of the earlier filing data of, and priority to, that
    patent application entitled
    "Expandable Inter Vivos Tube," filed on Dec. 17, 2013
      and afforded Ser. No. 14/109,880, (JVilasi-002)
      which claimed,
  pursuant to 35 USC 120, as a continuation-in-part, the
    benefit of the earlier filing data of and priority to that
    patent application entitled
    "Expandable Inter Vivos Tube," filed on Oct. 29, 2012
      and afforded Ser. No. 13/662,552 (JVilasi-001)
      (abandoned), and claimed,
  pursuant to 35 USC 119, the benefit of the earlier filing
    date and priority to that patent application entitled
    "Expandable Inter-Vivos Tube," filed on Dec. 4, 2013
    and afforded Ser. No. 61/911,589, the contents of
    all of which are incorporated by reference, in their
    entirety, herein.

BACKGROUND

1. Field of the Invention

The present invention relates to the field of medical devices and, more particularly, to an expandable inter vivos tube.

2. Background of the Invention

Inter vivos tubes, such as endotracheal tubes, are used to provide gases to the lungs during surgery. For example, an endotracheal tube is inserted into the trachea with its distal tip advanced halfway toward the tracheal bifurcation to provide gases, such as oxygen and anesthetics to a patient, during surgery. The exposed portion of the endotracheal tube is then firmly taped to the patient's face to prevent undesirable movement.

To align the position of conventional endotracheal tubes, an inflatable cuff balloon, at the distal end of the endotracheal tube, is inflated to correspond to the inner diameter of a portion of the trachea, thereby centering, or otherwise positioning, the endotracheal tube within the trachea. The cuff balloon, however, does not completely obstruct the entire trachea; only the portion where it is anchored is obstructed. When the cuff balloon is inflated, confirmation of the expanded balloon's contact within the trachea is achieved and delivery of anesthetic gases is performed.

Because of various sized endotracheal tubes, it is preferable to at least make the outer diameter of the endotracheal tube closely proximate to the size of the glottis, or opening between the vocal cords, for selective positioning of the endotracheal tube at a predetermined dilation. Therefore, various sized tubes are used, and the anesthesiologist or nurse anesthetist must choose from a variety of sized tubes to insert in the patient. If nasotracheal intubation or tracheostomy tubes are required in present practice even smaller interior diameters (ID) tubes are used.

Conventional endotracheal tubes vary in size and are numbered according to an internal diameter (ID). For example, for children, tubes are measured at about 3.5 to 7 mm (millimeters) internal diameter and from 7 to 11 mm for an adult. The internal diameter in women varies in general from 7.0 to 8.5 mm ID and in men from 8 to 10 mm ID. Typically, an endotracheal tube size selected for each patient is empirically selected by the anesthesiologist based on the patient's gender, age and size.

Ideally, the endotracheal tube should approximate as closely as possible the glottic size of the patient. Since there is no way to estimate the glottic size prior to the administration of anesthesia, in the existing prior art endotracheal tubes, a distal inflatable cuff is incorporated into the present day endotracheal tube which, when inflated, compresses the tracheal wall, thus creating a closed circuit between the endotracheal tube inflow from the anesthesia machine and outflow from the patient's lung to the exhalation valve. When nasotracheal intubation or tracheostomies is necessary, the internal diameter of the endotracheal tube is even less than the normal size, which is selected for orotracheal intubation, even greater respiratory resistance is created.

As noted in "Clinical Anesthesia," 1989 Edition, J. B. Lippincott Company, edited by Paul Barash, MD, Bruce Cullen, MD, and Robert Stoelting, MD, "[e]ndotracheal tube resistance varies inversely with the tube size. Each millimeter decrease in tube size is associated with an increase in resistance of 25 to 100%. The work of breathing parallels changes in resistance. A one (1) mm decrease in tube size increases the work of breathing from 34 to 154%, depending on the ventilatory pattern".

Therefore, in existing prior art inter vivos tubes, the internal diameter is small, and the only large portion is the external cuff balloon. This makes it harder for a surgical patient to breathe through the small internal diameter of the existing endotracheal tubes, especially if the patient must breathe spontaneously without assistance.

In summary, the prior art uses a local, inflatable balloon at the distal portion of an endotracheal tube, which narrows the patient's air way at the vocal cord level and may damage the vocal chords of the patient, if not property installed.

Applicant's prior U.S. Pat. No. 3,968,800 dated Jul. 13, 1976 and U.S. Pat. No. 4,827,925 dated May 9, 1989 describe an adjustable endotracheal tube which is complex to expand, and which does not have flexibility in being adapted to varying sized tracheas of different patients. Applicant's other prior U.S. Pat. No. 4,722,335, dated Feb. 2, 1988, discloses an expandable endotracheal tube including two overlapping curved segments, which when joined together form a closed tube. Similarly, applicant's prior U.S. Pat. No. 5,647,358, dated Jul. 15, 1997, discloses an expandable inter vivos tube that provides for expansion of the tube along at least designated parts of the tube. However, the configuration may be conceptually possible but in practical terms, difficult to construct and maintain at present prices.

Hence, there is a need in the industry for an expandable inter vivos tube that is easy to construct, easy to install, expand and remove during a procedure while reducing construction and costs of construction.

SUMMARY OF THE INVENTION

It is therefore an object of the present invention to provide a flexible, expandable inter vivos tube that expands its internal diameter at the glottic region of the trachea, to make breathing easier for a surgical patient.

Another object of the flexible, expandable inter vivos tube of the present invention is to vary a size of the internal diameter (ID) of an endotracheal tube in order to reach the glottic size of the patient without the intervention of a distal inflatable cuff.

With the present invention, the distal cuff is unnecessary and the one size endotracheal tube would fit most all adult patients. The present invention is especially useful in nasotracheal intubations where normally an even smaller internal diameter tube would be selected by the anesthesiologist.

It is also an object of the present invention to provide an endotracheal tube that maintains a same thickness throughout, without tapering.

It is yet another object of the present invention to provide an inter vivos tube having an internal diameter that remains substantially consistent from a proximal end to a distal end.

Another object of the present invention is to provide a vessel for administration of anesthesia by means of a flexible expandable tube that can be positioned correctly without interrupting gas flow and/or organ activity of a surgical patient.

It is also an object of the invention to provide a tube that can operate as an artificial flexible expandable vessel, such as a segment of a blood vessel to replace clogged arteries, or as a permanent catheter duct for providing fluids to or from the body.

It is also an object of the present invention to provide an improved inter vivos tube that overcomes the disadvantages of the existing prior art expandable tubes.

The basic concept of the present invention is to equip an inter vivos vessel, such as an endotracheal tube, artificial blood vessel or other tube with a positioning mechanism that is activated from a proximal end of the vessel and allows exact positioning and reversible anchoring within a body cavity, such as the trachea. The expandable tubes discloses herein can also be utilized as esophageal dilators, laparoscopic tubes, etc.

In the endotracheal tube embodiment, exact positioning and anchoring provide the conditions to provide anesthetic gases at the target, namely to the bronchial tubes, and ultimately the lungs.

In the present invention, the endotracheal tube can be anchored in the internal diameter of a body cavity, such as the trachea. The tube is expanded in size by means of an axially and longitudinally extendable elements inserted within the opposite free ends of a cul-de-sac formed by an H-like element. The extendable member includes free ends that run substantially the longitudinally length of the intro vivos tube. The two free edges of the extendable (flexible) cylindrical body elements engage corresponding free ends of the H-shaped element, which is curved to complete the circumference of the flexible expandable endotracheal tube. The "H" segment also provides for the integrity of the tube and, is constructed of a more rigid plastic than the rest of the tube itself. The remainder of the endotracheal tube utilizes the same or similar semi-rigid materials used in conventional inter vivos tubes. Polyvinyl tubes are presently used and continue to be used with varying degrees of hardness.

Moreover, upon extubation of the inter vivos tube of the present invention, retraction of the diameter of the tube is not required. By axially shifting the segmented arches away from each other at the free ends of the tube within the cul-de-sac of the "H" shaped element, the segmented arches are expanded so that the size of the endotracheal tube is increased and anchored during the administration of anesthesia. The segmented arches can be spread axially and longitudinally away from each other by injecting gas (or air) or fluid such as (saline) with a syringe connected to a one way valve and tube inserted in the lumen of a longitudinal canal within the rib of the "H".

The free ends of the flexible interrupted cylindrical tube are axially and longitudinally displaced away from each other so that the internal diameter of the endotracheal tube is expanded to anchor the tube within a body cavity, such as the trachea. One or more entry points may be used to provide fluid (gas, air, liquid) within a selected longitudinally extending rib of the "H" like element. The entry point(s) are also within a canal location in the wall on the expandable tube.

The longitudinal rib within the "H" is pierced at two or more levels along the course of the "H" element in order to distribute the fluid (gas, air, liquid) to substantially the length of the tube substantially uniformly.

It is important to note an expandable membrane is sealed to the inner and outer surfaces of the "H" element and also completely surrounds the free ends of the H-shaped element. However, the portion of the membrane that surrounds the free arms of the "H" will allow the opposite free longitudinal ends of the endotracheal tube to remain inserted within the cul-de-sac formed by the free arms of the "H" element. When a fluid is injected into a longitudinal channel within a rib of the "H", the two free ends of the endotracheal tube will slide substantially evenly apart to a desired expansion.

In another aspect of the invention, an optional non-expandable membrane can be fused along the entire length of the outer part of the "H" element and on the two expanding arms of the endotracheal tube longitudinally at a distance away from the free arms of the "H" element equal to the depth of the cul-de-sac. In this manner the tube cannot over expand.

In another aspect of the invention, the entire endotracheal tube can, itself, be sealed by a condom-like membrane to maintain smoothness and to help maintain the integrity of the tube itself.

According to an embodiment of the invention, the free end of one side of the cylindrical body, or segmented arch, can be moved, and the opposite side would be firmly attached inside the other free end of the H-shaped element. By means of the self-acting spreading of the endotracheal tube after insertion, the position of the endotracheal tube is maintained so that controlled anesthesia can be performed without gas regurgitation.

In another embodiment of the invention, the free ends of the "H" element may include a retaining or locking point that engages saw-tooth means or serrations in the extendable elements inserted within the free ends of the cul-de-sac formed by the "H" element. The engagement of the retaining point of the free-end of the "H" element and the serrations in the extendable elements lock the extendable element in an extended position.

In this embodiment of the invention, an expandable tube (referred to as an expander tube) may be inserted into the inter vivos tube in order to expand the extendable elements of the inter vivos tube to a desired position. The expander tube may then be removed after a desired expansion of the inter vivos tube is achieved. The expander tube may be reused, if desired, after sterilization.

In another embodiment of the invention, the retaining point of the free end of the "H" element may be hinged to lock the extendable elements to remain in the expanded mode.

In one embodiment of the invention, an inter vivos system is disclosed which comprises an expandable inter vivos tube comprising: a longitudinal H-shaped member comprising: an arched outer member; an arched inner member; a rib member connecting, at a substantial midpoint of said arched outer member and said arched inner member, said arched outer member, said arched inner member and said rib member forming first and second cavities, respectively; a retaining pin positioned on a free end of one of said arched outer member and said arched inner member, said retaining pin projecting into an opening of a corresponding one of said first and second cavities, and a flexible tube split along a longitudinal axis, said split forming first and second free ends, said first and second free ends engaging corresponding ones of said first and second cavities, wherein each of said first and second free ends include at least one serration, said at least one serration engaging said retaining pin, wherein flexible tube and said arched outer member having a radius forming said inter vivos tube with a substantially circular cross-section; and an expansion means comprising: a hollow tube member including a plurality of egress points along a longitudinal axis of said tube; and an expandable member attached to said proximate end and to said distal end of said tube member; wherein said tube member is sized to fit within an inner diameter of said expandable inter vivos tube.

In another embodiment of the invention, an inter vivos tube comprising a H-shaped member, as previously described, extends along a longitudinal axis of a tube member, wherein free ends of the tube member are contained within corresponding cavities or cul-de-sacs formed by the H-shaped member. Within each cavity is a self-contained expandable condom (e.g., a balloon) having an integrated air tube extending through one of an upper member of the H-shaped member and a lower member of the H-shaped member. The expandable condom may be filled with a fluid (gas, air, liquid), to expand the condom and displace the free ends of the tube member toward a free end of the H-shaped member. In one aspect of the invention, the rib member may be formed in a wedge wherein a width of the rib member at a distal end of the inter vivos tube is greater than a width of the rib member at a proximal end of the inter vivos tube. In another aspect of the invention, the condom may be composed of a material having different degrees of elasticity from its proximal end to its distal end. The variable degrees of elasticity allow the condom to expand at different rates as a fluid (i.e., gas or liquid) is injected into the condom. In another aspect of the invention, the distal end and the proximal end of the inter vivos tube are plugged or sealed to force the expanding condom to expand in a lateral direction rather than in a longitudinal direction, with respect to the inter vivos tube.

The inter vivos tube of the present invention, advantageously, expands substantially uniformly along its entire axial length, as fluid (gas, air, liquid) is pumped from a syringe into expansion lumens within the rib of the "H" or by the insertion of an expander tube.

BRIEF DESCRIPTION OF THE DRAWINGS

The advantages, nature, and various additional features of the invention will appear more fully upon consideration of the illustrative embodiments to be described in detail in connection with accompanying drawings wherein like reference numerals are used to identify like element throughout the drawings.

Figure 1:
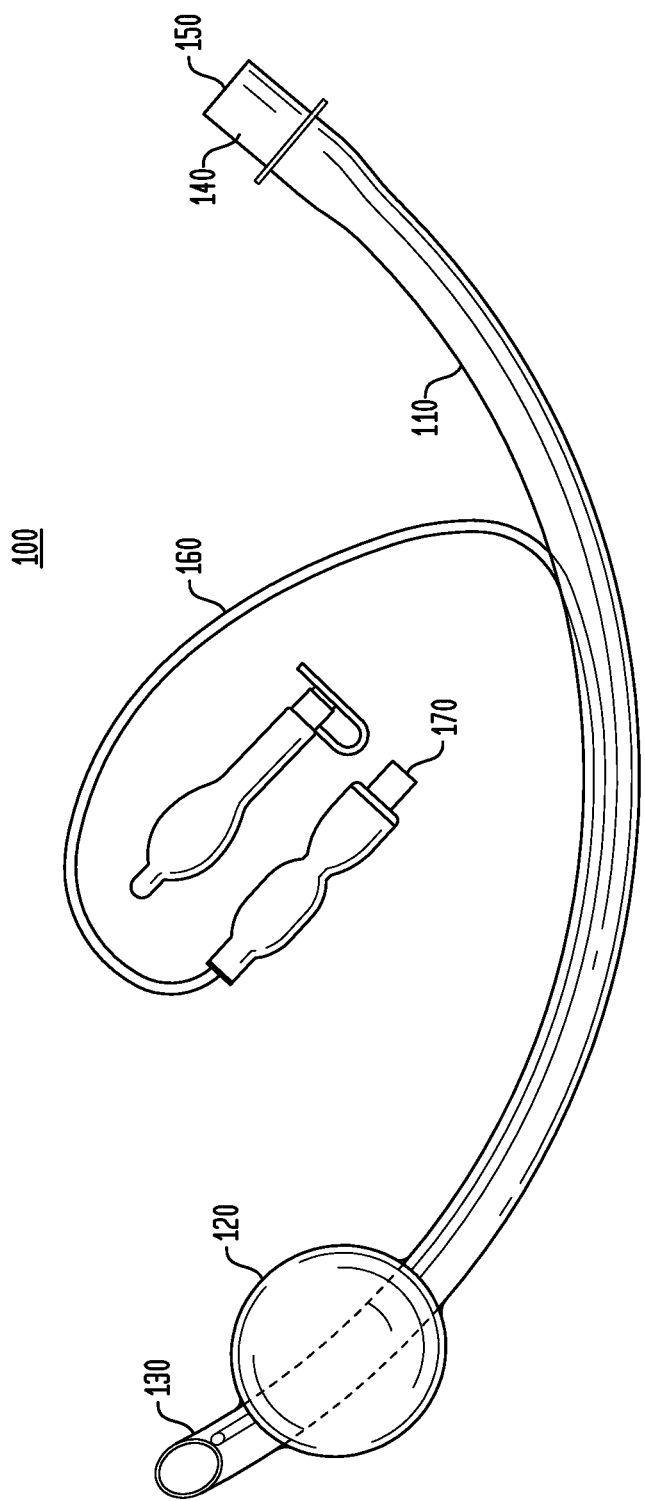
FIG. 1 illustrates a perspective view of conventional endotracheal tube with an expanded distal cuff which compresses distally against the tracheal wail.

It is noted that the drawings of the invention are not to scale. The drawings are intended to depict only typical aspects of the invention, and therefore should not be considered as limiting the scope of the invention. In the drawings, like numbering represents similar or like elements between the drawings.

It is to be understood that the figures and descriptions of the present invention described herein have been simplified to illustrate the elements that are relevant for a clear understanding of the present invention, while eliminating, for purposes of clarity many other elements. However, because these elements are well-known in the art, and because they do not facilitate a better understanding of the present invention, a discussion of such element is not provided herein. The disclosure herein is directed also to variations and modifications known to those skilled in the art.

DETAILED DESCRIPTION OF THE PRESENT INVENTION

FIG. 1 illustrates a conventional endotracheal tube (i.e., inter vivos tube) 100 represented as an elongated tube 110 having a bulb member 120 positioned on a distal end 130 and a connection member 140 on a proximate end 150. The connection member 140 on proximate end 150 provides a means for allowing gases to flow through inter vivos tube 100 to distal end 130. Bulb member 120, which is shown in an expanded position, seals a passageway (not shown) into which inter vivos tube 100 is inserted to prevent gases exiting the distal end 130 from escaping along the inter vivos tube 100.

FIG. 1 further illustrates a smaller tube 160 running along an inner edge of inter vivos tube 100. Tube 160 may be used to provide a fluid, e.g., air or liquid, to bulb member 120 so as to expand bulb member 120 to the illustrated inflated position. Tube 160 may be connected to an air or liquid supply (not shown) by connection member 170.

Figure 2:
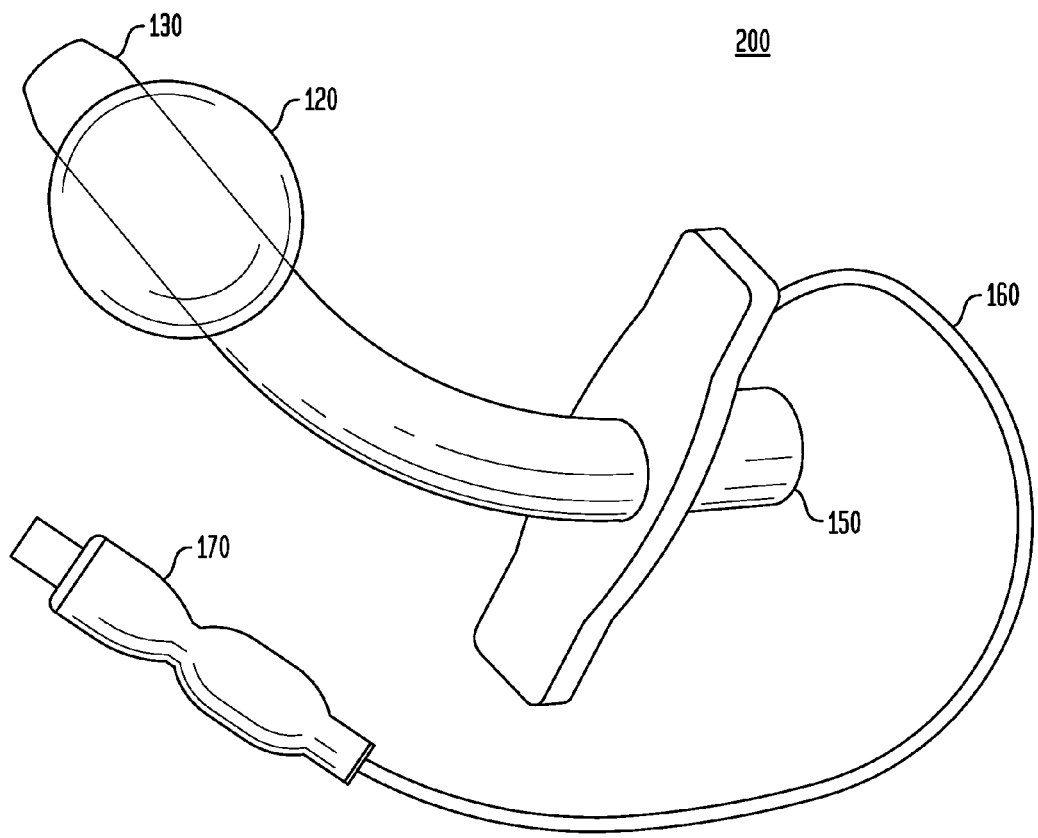
FIG. 2 illustrates a perspective view of a conventional tracheostomy tube inflated distally in the same manner, as in FIG. 1.

FIG. 2 illustrates a conventional tracheostomy tube (i.e., inter vivos tube) 200 used in providing air to a patient undergoing a tracheostomy process. Inter vivos tube 200 operates in a manner similar to that of the inter vivos tube 100 shown in FIG. 1, wherein a bulb member 120, positioned at a distal end 130, is expanded to prevent a fluid (e.g., air or liquid) injected from the proximate end 150 from escaping along the inter vivos tube 200. A fluid, such as air or liquid, enters through connection member 170 to expand bulb member 120, as previously discussed.

Figure 3:
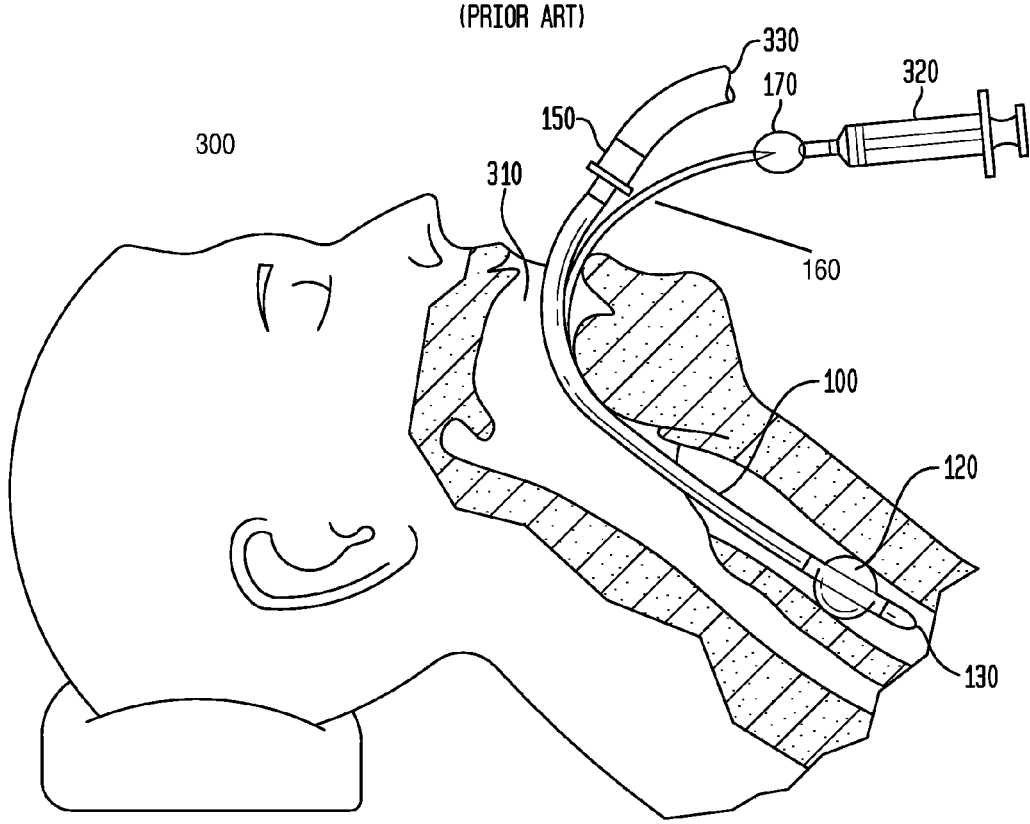
FIG. 3 illustrates a perspective view of a conventional endotracheal tube inserted through the vocal cords and expanded within the trachea.

FIG. 3 illustrates a cross-sectional view 300 of the insertion and positioning of a conventional endotracheal tube 100 through a patient's vocal cords. As shown, bulb member 120 is an expanded mode to seal the patient's air passage 310. Also shown is syringe 320 that is connected to connection member 170 that represents a means for providing fluid to bulb member 120 so as to expand bulb member 120 to seal air passage 310. Also shown is tube 330 that is connected to proximate end 150 to allow a fluid (e.g., gas, air, liquid) to pass from proximate end 150 of the inserted endotracheal tube 100 to distal end 130 of the inserted endotracheal tube 100.

Figure 4:
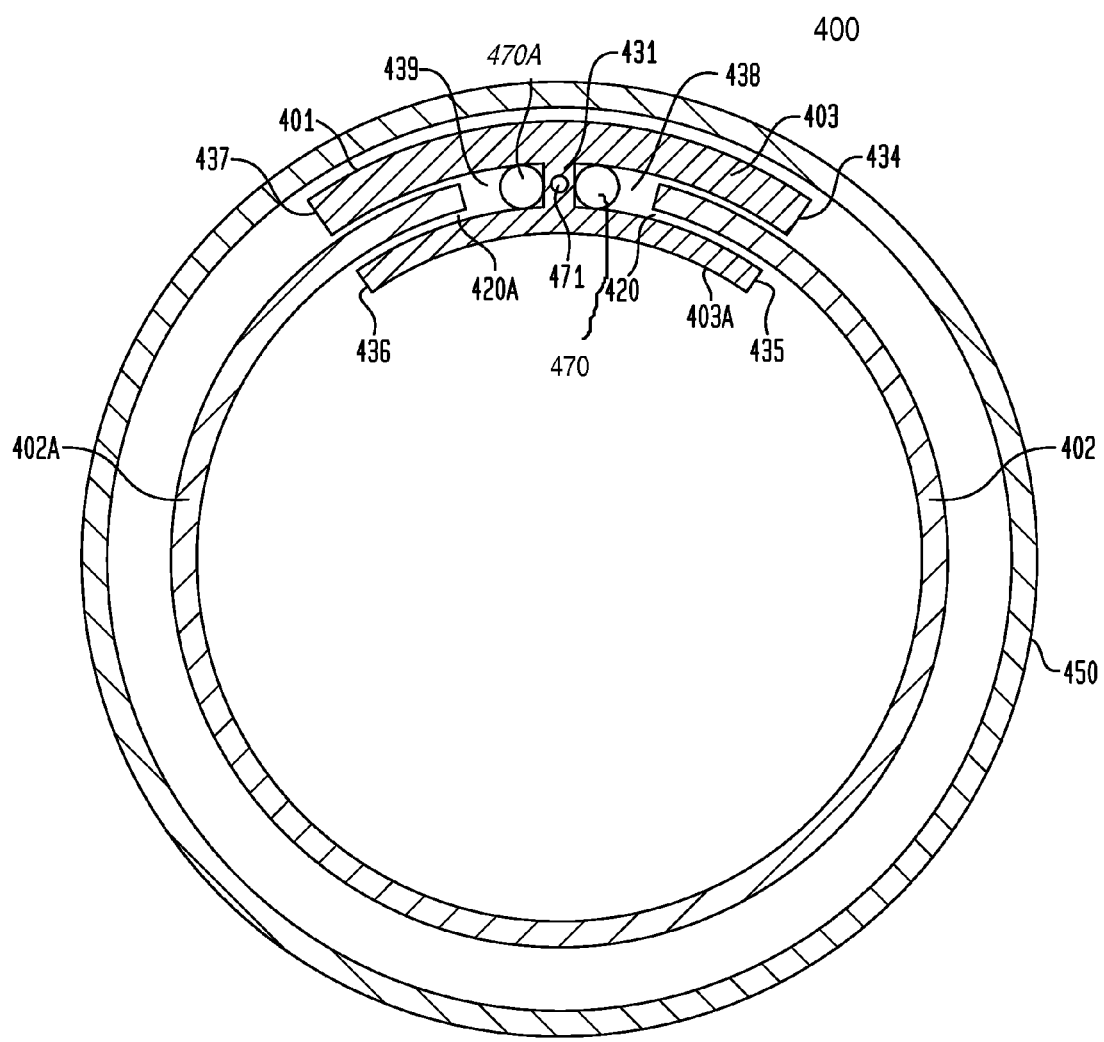
FIG. 4 illustrates a cross-sectional view of a first aspect of inter vivos tube in accordance with the principles of the invention.

FIG. 4 illustrates a cross-sectional view of an exemplary inter vivos tube 400 in accordance with the principles of the invention. As shown, inter vivos tube 400 includes an H-shaped member 401 extending substantially longitudinally along an edge of inter vivos tube 400. The H-shaped member element 401, operating as a spine of said inter vivos tube 400, comprises an arched outer element 403 (outer circumference element) and an arched inner element 403A (inner circumference element) arranged circumferentially opposite each other at equal angles to each other along a circumference of the flexible expandable inter vivos tube 400. The H-shaped connection 401 includes rib 431, which represents the cross-bar of the "H" in the H-shaped connection member 401, joining at a substantial midpoint the arched elements 403 and 403A. The H-shape connector elements 403 and 403A, taken with rib 431, also form cul-de-sac receptacle cavities 438 and 439, respectively. The cul-de-sac or cavities 438 and 439 have an opening that is sized to receive, in tongue-in-groove-like fashion, free end tongue portions 420 and 420A of arched tube segments 402 and 402A, respectively. The H-shaped connector member 401 has respective free ends 434, 435 that define cavity 438 and free ends 436 and 437 that define cavity 439. Outer curved or ached element 403 is longer than inner curved arched element 403A to accommodate an increase in circumference.

Rib 431 connects the arched elements 403, 403A of H-shaped connecter member 401 and provides rigidity and structural integrity for the inter vivos tube 400. The rigidity of rib 431 has sufficient flexibility to enable the inter vivos tube 400 to be inserted into the trachea of the patient and to substantially conform to the patient's airway, while retaining sufficient rigidity to permit a medical worker to position, and to insert, the tube 400 against anatomical resistance of the patient's throat and airway structures (e.g., the vocal cords). Rib 431 may also include longitudinal conduit 471 for accepting a fiber optic cable for a view-0-scope enablement.

The H-shaped connector member may be made of a material such as polyvinyl chloride plastic, to provide sufficient rigidity and flexibility.

Tongues 420, 420A of arched tube elements 402, 402A, respectively, are normally in a retracted position within corresponding cavities 438, 439, providing inter vivos tube 400 with a minimum diameter.

Although not shown, it would be appreciated that the diameter of inter vivos tube 400, along an axis substantially perpendicular to the arched tube elements 402, 420A increases when tongues 420, 420A are forced circumferentially apart by entrance of a fluid pumped into the respective cavities 438, 439. Hence, the cross sectional profile of the inter vivos tube 400, in accordance with the principles of the invention, is one of substantially circular in an unexpanded mode and of an elliptical in an expanded mode.

The increased diameter of the inter vivos tube 400, caused by the displacement of the tongue elements 420, 420A, of corresponding arched segments 402, 402A, causes the passageway (FIG. 3, 310) into which the inter vivos tube 400 is inserted to become blocked, such that air may only enter or exit the passageway through the internal diameter formed by the inter vivos tube 400.

In addition, the cavities 438, 439 and tongues 420, 420A are sized to prevent tongues 420, 420A from expanding to a distance that would cause tongues 420, 420A to exit cavities 438, 439.

Also, shown is an, optional, expandable membrane 450 that surrounds inter vivos tube 400. Optional membrane 450 may be composed of a material that provides for a smooth surface of the inter vivos tube 400. The optional membrane 450 may be composed of a material such as PVC (polyvinyl chloride) that allows for a smooth entry and exit of the inter vivos tube 400 into and out of a passage way (e.g., FIG. 3, 310).

Also illustrated are balloons 470, 470A incorporated into cavities 438, 439, respectively. Balloons 470, 470A expand as fluid (gas, air, liquid) is injected into balloons 470, 470A through the H-shaped connection member 401, as will be described in further detail.

Figure 5:
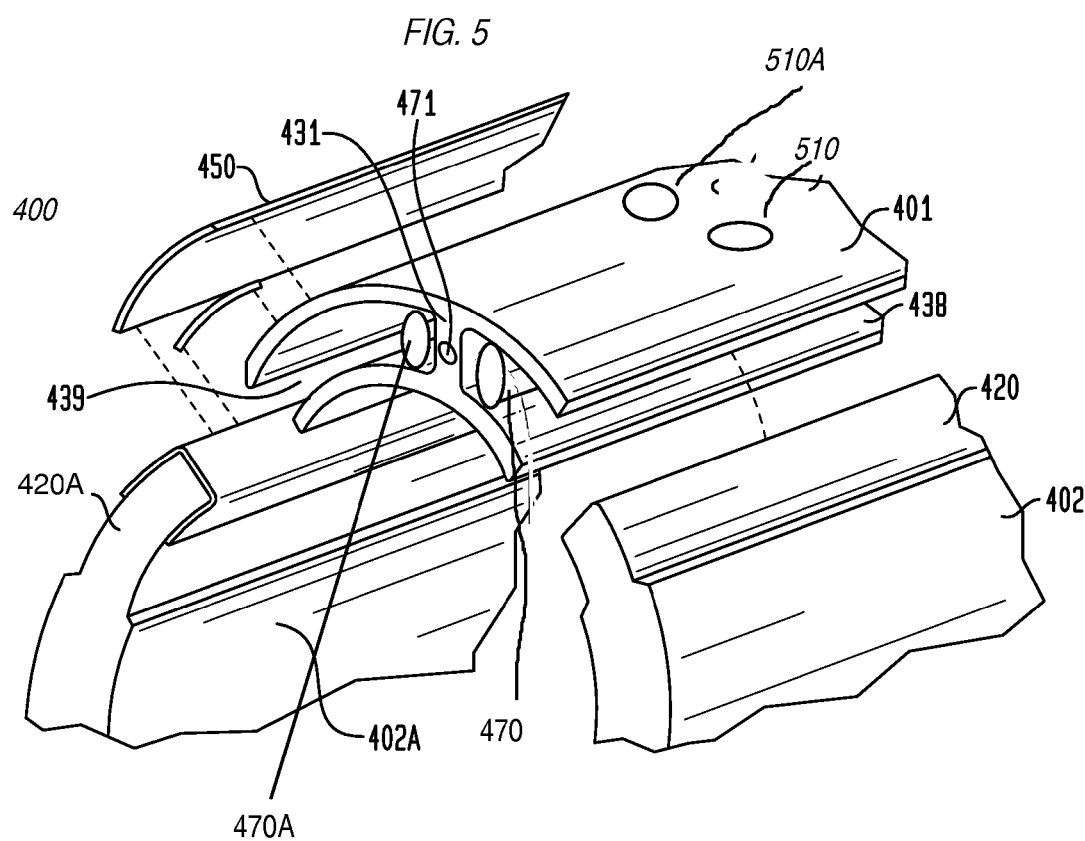
FIG. 5 illustrates perspective exploded views of inter vivos tube in accordance with a first embodiment of the invention.

FIG. 5 illustrates an expanded perspective view of the inter vivos tube 400 shown in FIG. 4, wherein balloons 470, 470A, are incorporated into cavities 438, 439, respectively.

Also illustrated in inter vivos tube 400 is insertion or ingress points 510, 510A incorporated in an outer surface of H-shaped connecter member 401. Insertion points 510, 510A allows entry of a fluid (e.g., air, gas, saline solution, etc.) into corresponding balloons 470, 470A.

In this illustrated case, fluid (gas, air, liquid) is injected into insertion point 510, 510A exits directly into balloons 470, 470A to displace tongues 420, 420A so as to increase the circumference of inter vivos tube 500 by increasing the diameter between the arched segments 402, 402A. That is, tongues 420, 420A, when displaced, so as to be positioned in an expanded mode, causes the shape of inter vivos tube 400 to be oblong or elliptical rather than a substantially circular shape when tongues 420, 420A are in an unexpanded state.

Although not shown, it would be appreciated that a proximal end and a distal end of H-shaped connector member 401 may be sealed. Thus, a sealing means (e.g., plugs) may be positioned at a proximate end and a distal end of cavities 438, 439. In this case, as a fluid (e.g., air, gas, liquid) is injected into injection point 510, 510A and exits into corresponding balloons 470, 470A, the space in cavities 438, 439 becomes filled with the expanded balloon 470, 470A and tongues 420, 420A are displaced from cavities 438, 439. Hence, a diameter of the inter vivos tube 400 increases as tongues 420, 420A are displaced from cavities 438, 439, respectively. As would be appreciated the sealing of the distal end and proximal end may be an optional embodiment as the balloons 470, 470A represent a self-contained sealed structure that retains the injected fluid. Although plugs are described as sealing means it would be recognized that the sealing means may be integrated into the H-shaped member 401. For example, a distal end 130 and a proximal end 150 of H-shaped member 401 may be heat-sealed such that the outer arch segment and the inner arched segment are joined together. Alternatively, flaps may be attached (heat, adhesive) onto the distal end 130 and the proximal end 150 in order to provide a closed cavity 438, 439.

Figure 6:
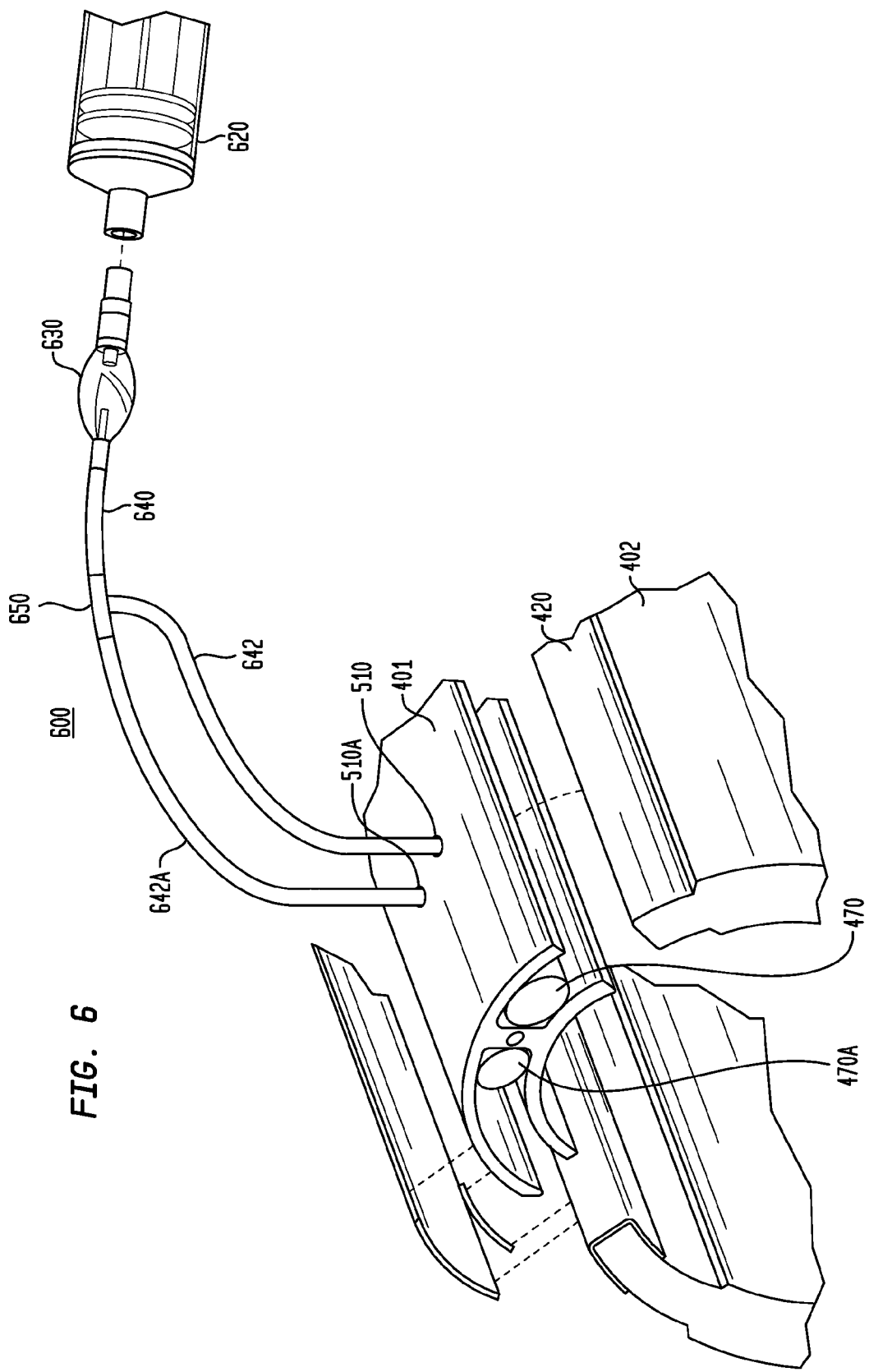
FIG. 6 illustrates a perspective view of a means for causing expansion of the inter vivos tube shown in FIG. 4.

FIG. 6 illustrates perspective view of the exemplary embodiment of the endotracheal tube 600 shown in FIGS. 4 and 5 in accordance with the principles of the invention.

In this illustrated example, a fluid, e.g., air, is injected by a syringe 620, for example, through tube 642, 642A inserted into insertion points 510, 510A, respectively. Y-connector 650 divides the air injected by syringe 620 into tube 640 into tubes 642, 642A, which then enters and inflates balloons 470, 470A, respectively. The injection process further includes a one-way valve 630 that allows the fluid to pass through tube 640 into H-shaped connection member 401, through injection points 510 and 510A. The injected air enters balloon 470, 470A to displace tongues 420, 420A to expand the diameter of the inter vivos tube 400. One way valve 630 allows the fluid to pass in a first direction to displace tongues 420, 420A and to statically retain the injected fluid until the valve is released. In this released state, tongues 420, 420A may retract into cavities 438, 439 to reduce the size of the inter vivos tube 400 to its minimum size.

Figure 7:
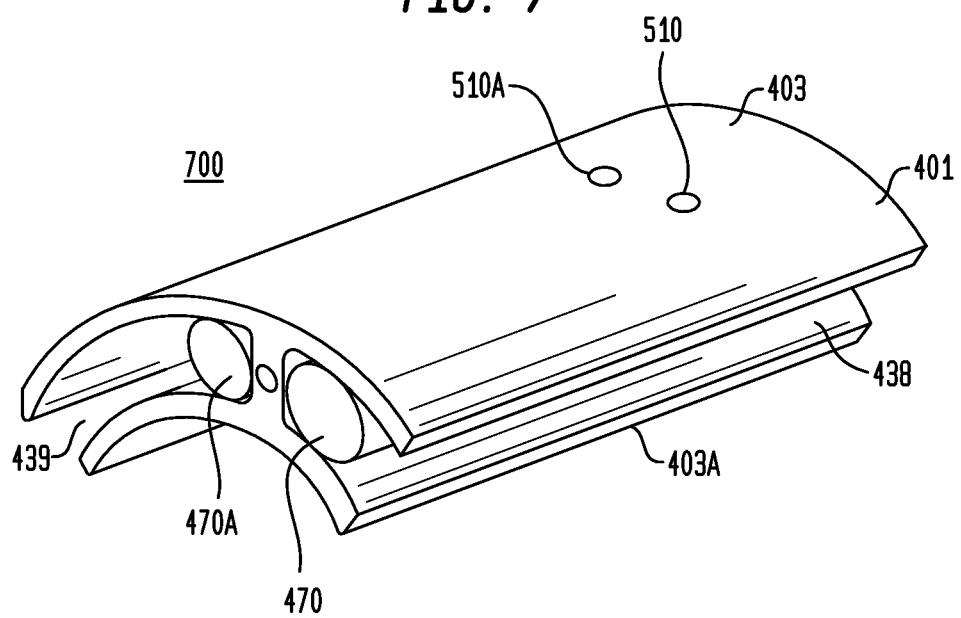
FIG. 7 illustrates a perspective view of inter vivos tube in accordance with a second embodiment of the invention.

FIG. 7 illustrates a perspective view of a second aspect of an inter vivos tube 400 in accordance with the principles of the invention. In this exemplary embodiment, balloons 470, 470A, which are shown in an expanded state, are incorporated into cavities 438, 439, respectively. In this aspect of the invention, balloons 470, 470A may be constructed of a material that has a substantially uniform elasticity, wherein the balloons expand substantially uniformly as air enters (in this illustrative example) a proximal end of the balloon 470, 470A through air tubes 642, 642A (not shown) that are placed in injection ports 510, 510A (see FIG. 6). In this case, tongues 420, 420A are displaced from cavities 438, 439 in a substantially uniform manner, as previously described.

In another aspect of the invention, balloons 470, 470A may be constructed of a material having a variable degree of elasticity, which allows portions of balloons 470, 470A to expand at different rates. For example, the elasticity of the material of balloons 470, 470A may be such that a distal end of balloons 470, 470A may expand faster than a proximal end of balloons 470, 470A. In this manner, a distal end of the inter vivos tube 400 may expand to a wider opening than at the proximal end, as the distal end of balloons 470, 470A expand the distal ends of corresponding tongues 420, 420A faster than the proximal ends of tongues 420, 420A.

In one aspect of the invention, balloons 470, 470A may be constructed of a stretchable material wherein a thickness of the stretchable material is less at a distal end than a proximal end, resulting in a greater degree of elasticity at the distal end than at a proximal end. In another aspect of the invention, the coefficient of elasticity of the material of balloons 470, 470A may be varied from the distal end to the proximal end to allow greater stretchability at the distal end than the proximal end.

Figure 8A:
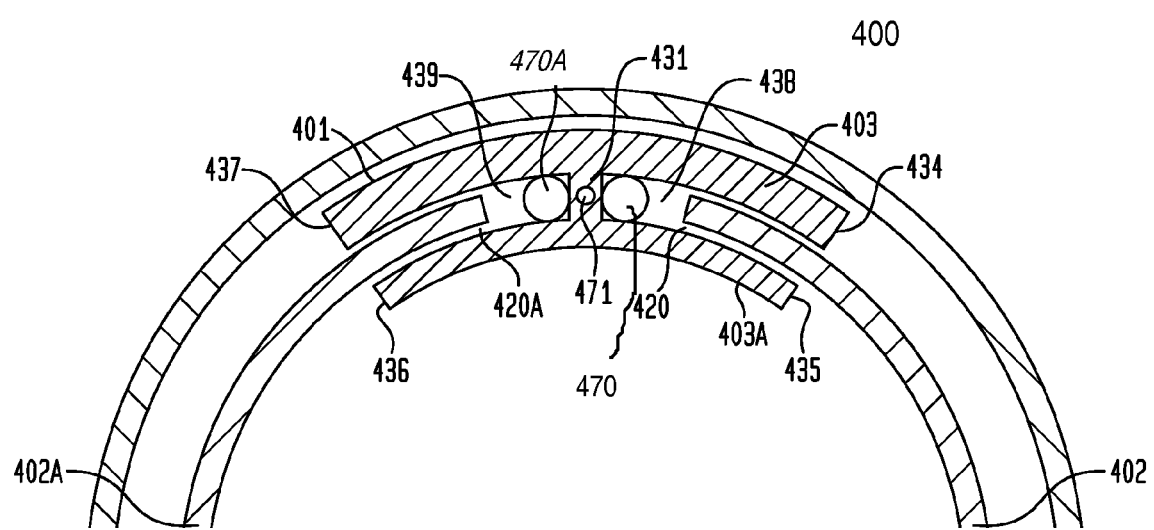
FIG. 8A-8B illustrate cross sectional-views of a distal end and a proximal end of an inter vivos tube in accordance with the principles of the invention.
Figure 8B:
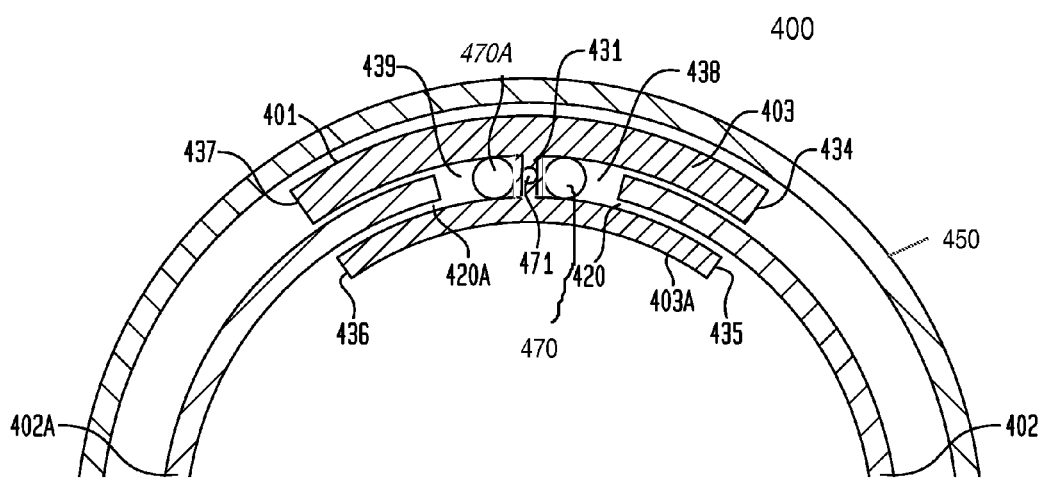

FIGS. 8A-8B illustrate cross sectional views of a distal end and proximal end, respectively, of an inter vivos tube in accordance with another aspect of the invention. In this illustrative example, the width of rib 431 at the distal end (FIG. 8A) is wider than the width of rib 431 at the proximal end (FIG. 8B).

In this illustrative aspect of the invention, balloons 470, 470A, are offset within H-shaped member 401 such that as a fluid (air, water, gas) is injected into balloons 470, 470A, through tubes 642, 642A, respectively, a distal end of inter vivos tube 400 has a wider opening than a proximal end of inter vivos tube 400. The greater width of the vivos tube 400 at the distal end being caused by the wedge shape design of rib 431.

As an illustrative example, an inter vivos tube 400 having a width rib 431 of the proximal end of 3.5 mm and a width of rib 431 at the distal end being 6.5 mm, then the expansion of balloons 470, 470A to a lateral diameter of 1.0 mm would create an expanded inter vivos tube 400, in accordance with the principles of the invention, with a distal end of 8.5 mm and a proximal end of 5.5 mm. As would be appreciated the outer and inner arched members 403, 403A are sized to prevent tongues 420, 420A from exiting cavities 438, 438A, as previously discussed. Alternatively, the balloons 470, 470A may be sized to have a maximum expansion that limits the expansion of tongues 420, 420A.

In accordance with this aspect of the invention, the expansion of the inter vivos tube about the vocal cord area, which is the smallest area in the trachea, is smaller than the expansion of the inter vivos tube 400 in the trachea, itself. Hence, there is less trauma experienced on the trachea, as the expansion of the inter vivos tube 400 engages the non-capillary vocal cord area prior to engaging the trachea.

In addition, the larger expansion of the distal end of the inter vivos tube 400 maintains a steady flow of gas through a larger opening (at least 5.5 mm in the example above).

Although the exemplary inter vivos tube shown 400 above has been described with a particular configuration, it would be appreciated that the size of the distal and proximal ends of the rib 431 and the expansion capability of balloons 470, 470A may be altered without altering the scope of the invention.

Returning to FIG. 4, in another aspect of the invention, the H-shaped member 401 may be structured such that the inner circumference member 403A is thinner than the outer circumference member 403. In this aspect of the invention, the inner circumference member 403A has a reduced profile within inter vivos tube 400, thus, increasing the effective area for the flow of gas through inter vivos tube 400.

Figure 9:
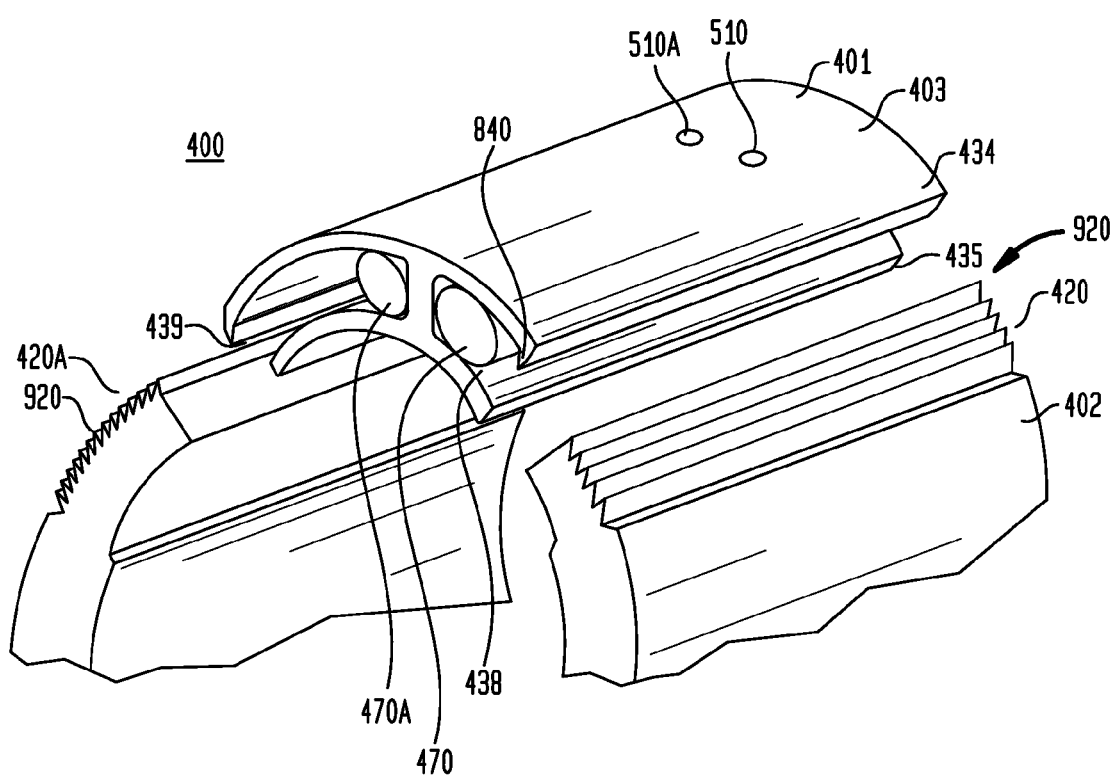
FIG. 9 illustrates a perspective view of inter vivos tube in accordance with another embodiment of the invention.

FIG. 9 illustrates another aspect of the inter vivos tube 400 in accordance with the principles of the present invention. FIG. 9 illustrates a retaining pin 940 extending from an end 434 of outer arched member and slightly decreasing the opening of cavity 438. A similar retaining pin 940 is shown slightly decreasing the opening of cavity 439. Also illustrated is a plurality of serrations 920 impressed on tongues 420, 420A. Retaining pins 940 engage one of the plurality of serrations 920 on corresponding tongues 420, 420A as tongues 420, 420A are displaced from cavities 438, 439, respectively, by the expansion of balloons 470, 470A.

Retaining pins 940 prevent tongues 420, 420A from retracting back into cavities 438, 439 after tongues 420, 420A have been expanded (or displaced from cavities 438, 439).

In one aspect of the invention, retaining pins 940 may be incorporated only along a portion of the H-shaped member 401, to limit only a portion of tongues 420, 420A from retracting into cavities 438, 439. For example, retaining pins 940 may be positioned along a portion of inter vivos tube 400 extending from the proximal end of inter vivos tube 400. In this case, the proximal end of inter-vivos tube is non-retractable while the distal end of inter vivos tube 400 is retractable as balloons 470, 470A are deflated. FIG. 9, may, for example, illustrate a portion of the inter vivos tube 400 near the proximal end. While balloons 470, 470A extend substantially from the proximal end of inter vivos tube 400 to the distal end of inter vivos tube 400, the retaining pin 940 may extend a limited distance from the proximal end of inter vivos tube 400.

Figure 10A:
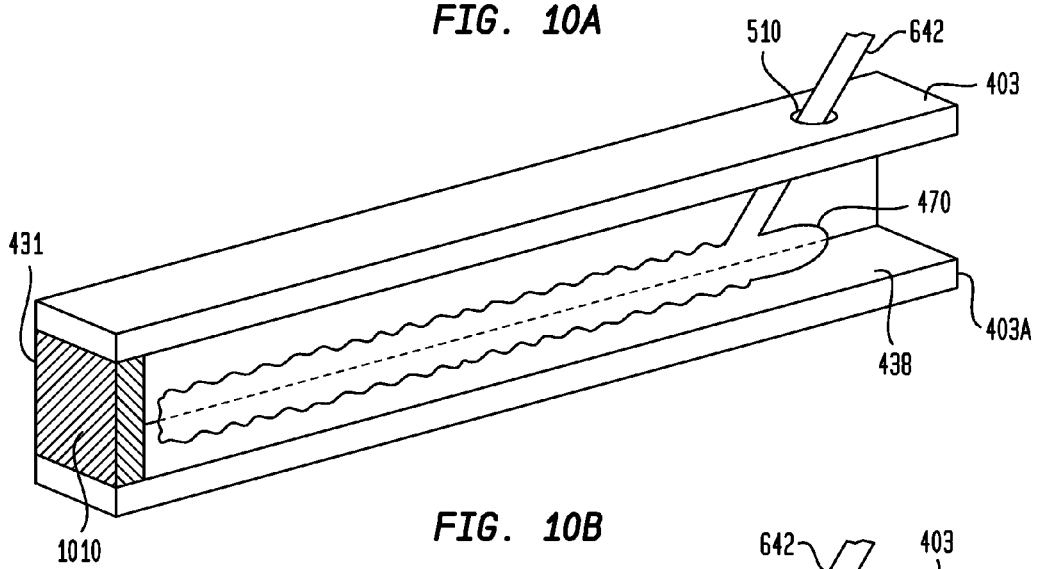
FIGS. 10A-10C illustrate an exemplary embodiment of a balloon structure in accordance with the principles of the invention.
Figure 10B:
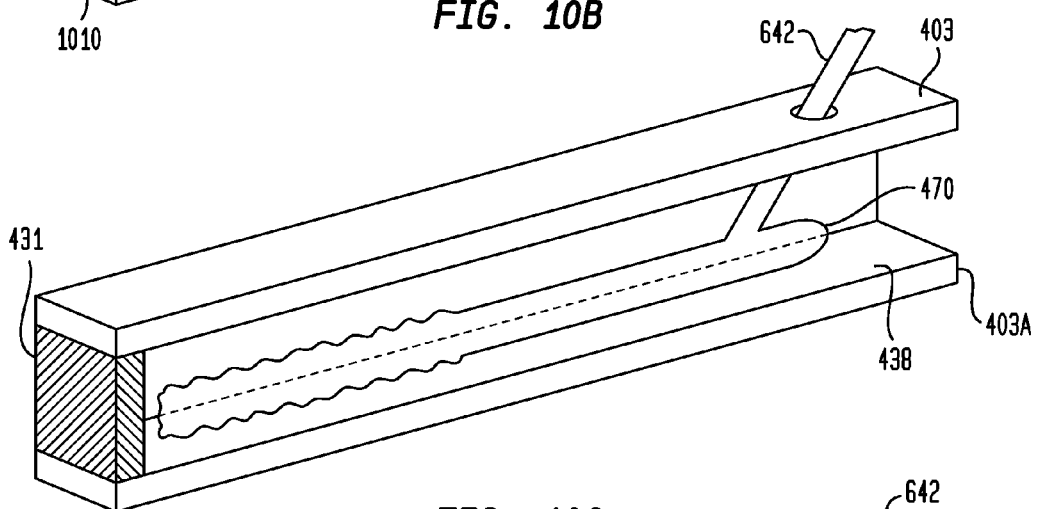
Figure 10C:
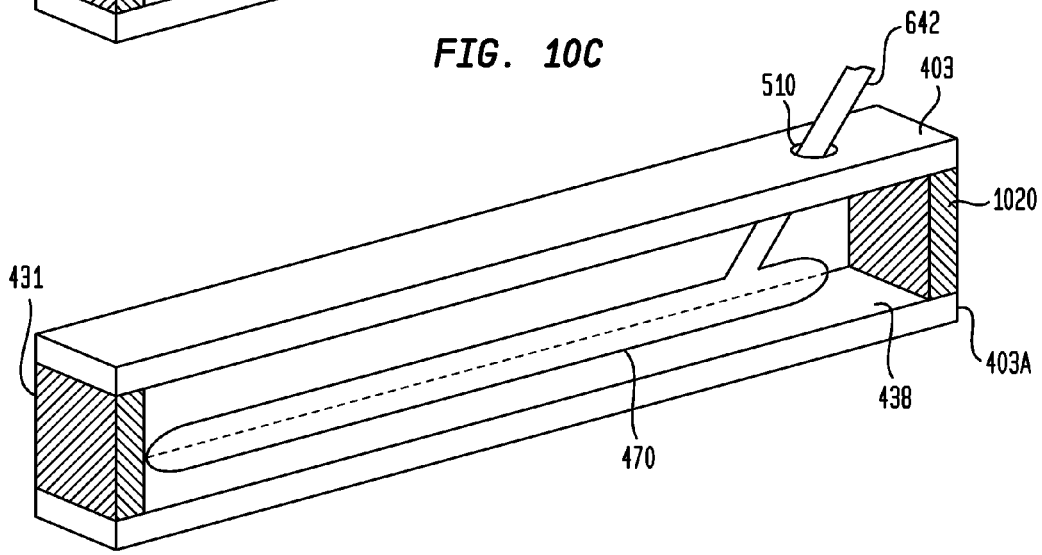

FIGS. 10A-10C illustrate an exemplary embodiment of balloon 470 in different degrees of inflation. FIG. 10A illustrates an example of balloon 470 in cavity 438 in a deflated state, wherein tongue 420 (not shown) is in a retracted state. Although not shown it would be appreciated that balloon 470A in cavity 439 would have a similar configuration and operation as discussed, herein, with regard to FIGS. 10A-10C.

Figure 11:
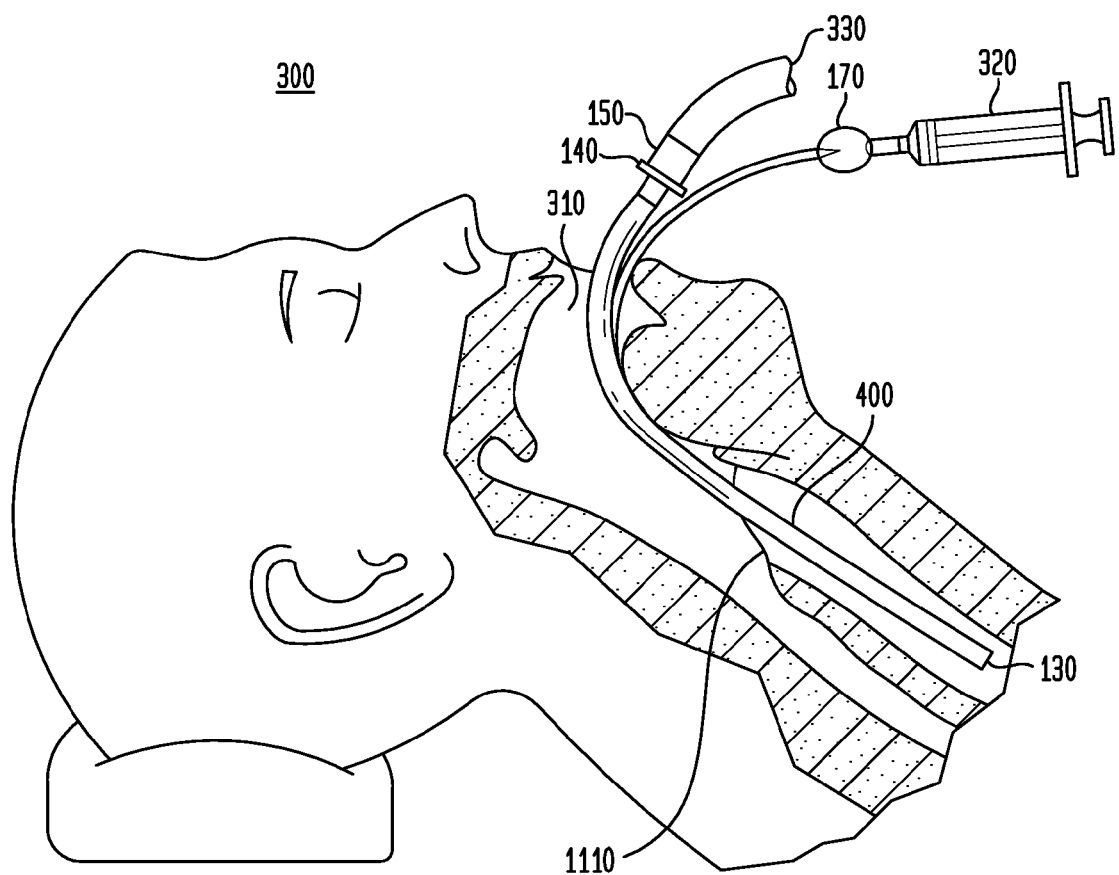
FIG. 11 illustrates an exemplary application of the inter vivos tube in accordance with the principles of the invention.

In this illustrative aspect, tube 642, extended through ingress port 510, is shown integrated into a proximal end of balloon 470. Ingress port 510 is substantially close to a proximal end of inter vivos tube 400. As would be appreciated, the ingress port 510 is positioned such that a connector may be attached to the proximal end of inter vivos tube 400. See for example, FIG. 3 or 11, wherein tube 330 is connected to a proximal end of the inter vivos tube to allow a gas to pass through the inter vivos tube 100 (FIG. 3), 400 (FIG. 11). In one aspect of the invention, the connector may be an accordion type connector (see FIG. 13, ele. 1320) that allows flexibility in the attachment, and position of tube 330, onto connector 140 on the proximal end 150 of inter vivos tube 400 (see FIG. 11).

FIG. 10B illustrates an example of balloon 470 in cavity 438 in a semi-inflated state. In this illustrative aspect, fluid (e.g., air) is provided through tube 642 and distributed throughout balloon 470. Generally, balloon 470 may fill, and, thus, expand, from the point of entry of the fluid provided through tube 470. Alternatively, as previously discussed, balloon 470 may be composed of material having different degrees of elasticity and, thus, balloon 470 may expand beginning in the area when the degree of elasticity is greatest and as the pressure within balloon 470 increases, those areas having a lesser degree of elasticity begin to expand.

FIG. 10C illustrates an example of balloon 470 in cavity in an inflated state. In this illustrative aspect, balloon 470 is fully expanded such that tongue 420 (not shown) is displaced to an expanded state.

Although it has been shown that ingress port 510 (510A), and consequently tube 642 (642A), are positioned near a proximal end of inter vivos tube 400, it would be appreciated that ingress port 510 (510A) may be positioned near a distal end of inter vivos tube 400. In this alternative embodiment, tubes 642, 642A may extend along an outer surface of inter vivos tube 400 (or within the upper or lower arched segments 403, 403A). In a further alternative embodiment, ingress port 510, 510A may be incorporated into inner arch segment 403A at the proximal end or the distal end. In this case, tube 642 (642A) may be extend through the lower arched segment 403A of inter vivos tube 400.

Further illustrated is plug 1010 incorporated into a distal end of the H-shaped member 401 and plug 1020 incorporated into a proximal end of the H-shaped member 401. Plugs 1010 and 1020 limit the expansion of balloons 470, 470A in a lateral direction to displace tongues 420, 420A from cavities 438, 439, respectively. Although, plugs 1010 and 1020 are shown, it would be appreciated that the distal end and the proximal end of the H-shaped member may be sealed by a flap attached to each of the distal end and the proximal end (see, for example, FIG. 14, ele. 1420). The flap may be heat sealed or adhesively applied to the distal end and the proximal end. In a further alternative embodiment, the outer circumference member and the inner circumference member may be joined at each of the distal end and the proximal end of the H-shape member 401 to expand balloon 470, 470A in a lateral direction.

FIG. 11 illustrates an exemplary application of the inter vivos tube 400 in accordance with the principles of the invention. In this illustrative application, similar to that shown in FIG. 3, inter vivos tube 400 is inserted, and positioned through, a patient's vocal cords, into the trachea. As shown syringe 320, that is connected to connection member 170, represents a means for providing fluid to balloons 470, 470A (not shown) in inter vivos tube 400, so as to expand balloons 470, 470A (not shown) to seal air passage 310. Also shown, and as previously described, tube 330 is connected to connection member 140 on a proximal end 150 of inter vivos tube 400 to allow a fluid (e.g., gas, air, liquid) to pass from the proximate end 150 of the inserted inter vivos tube 400 to a distal end 130 of the inserted inter vivos (endotracheal) tube 400.

In one aspect of the invention, inter vivos tube 400 expands to engage vocal cords 1110, which represents a smallest opening within the tracheal passageway. The distal end of inter vivos tube 400, extending past the vocal cords 1110, further expands, at least to the size of the opening of the vocal cords (or larger). However, while the expanded distal end of inter vivos tube 400 may expand to a larger size, the expanded distal end 130 of inter vivos tube 400 may or may not engage or contact the walls of the trachea. When the expanded inter vivos tube 400 fails to contact the walls of the trachea, but the air passage is sealed at the vocal cords 1110, less trauma is experienced by the user.

Figure 12:
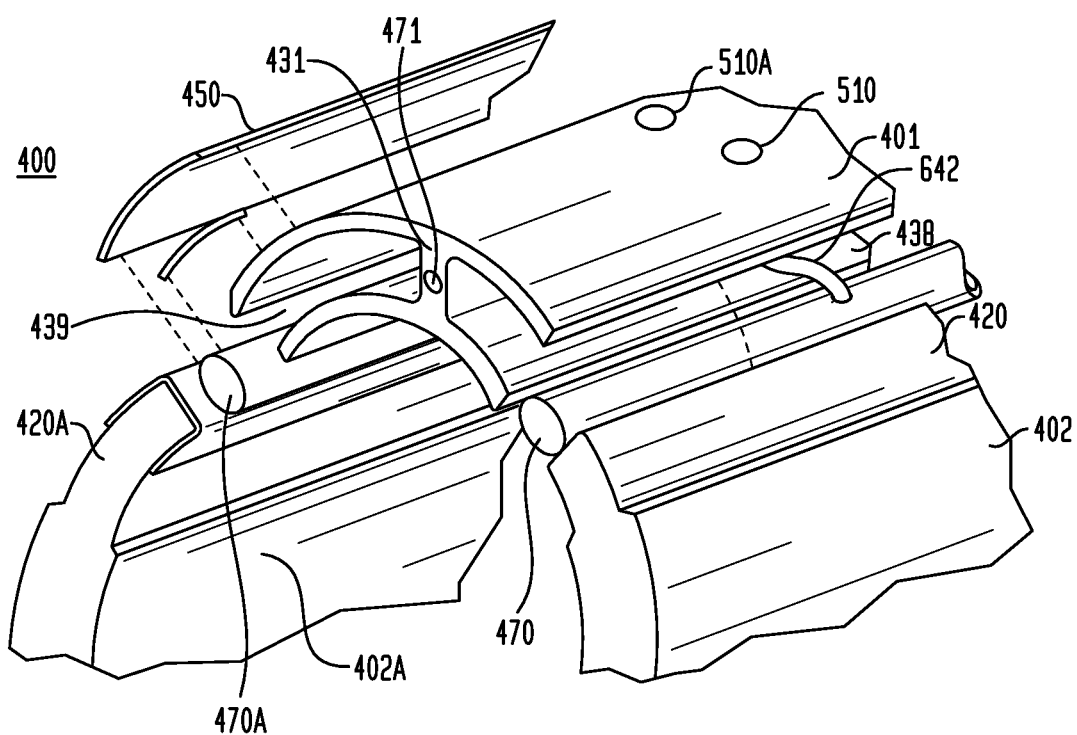
FIG. 12 illustrates a perspective view of a second embodiment in accordance with the principles of the invention.

FIG. 12 illustrates a perspective view of second embodiment of the inter vivos tube 400 in accordance with the principles of the invention.

In this illustrated embodiment, an H-shaped member 401 extends longitudinally along a longitudinal axis of inter vivos tube 400, as previously described. Similarly, H-shaped member includes an outer (upper) arched segment 403 and an inner (lower) arched segment 403A separated by rib 431, which is positioned substantially medially between the outer arched segment 403 and the inner arched segment 403A, as previously described. Also shown, are free ends 402, 402A of tube 400, including tongues 420, 420A, respectively. Tongues 420, 420A are retained, generally, in corresponding cavities 438, 439, formed by the outer arched segment 403, the inner arched segment 403A and rib 431, as previously described.

In this exemplary embodiment of the invention, balloons 470, 470A are attached to corresponding ones of free ends 420, 420A. Balloons 470, 470A include corresponding connection leads 642, 642A into which a fluid (e.g., air, liquid) may be injected into balloons 470, 470A. The connection leads leads 642, 642A may extend through injection or ingress ports 510, 510A as previously described.

As previously described, a distal end 130 and a proximal end 150 of the H-shaped member 401 of inter vivos tube 400 may be sealed to prevent balloons 470, 470A from expanding longitudinally. Sealing distal end 130 and proximal end 150 of H-shaped member forces expanding balloons 470, 470A to expand in a lateral direction and, thus, applying a force between rib 431 and tongue 420 (420A) in displace tongue 420 (420A) from cavity 438 (439).

Figure 13:
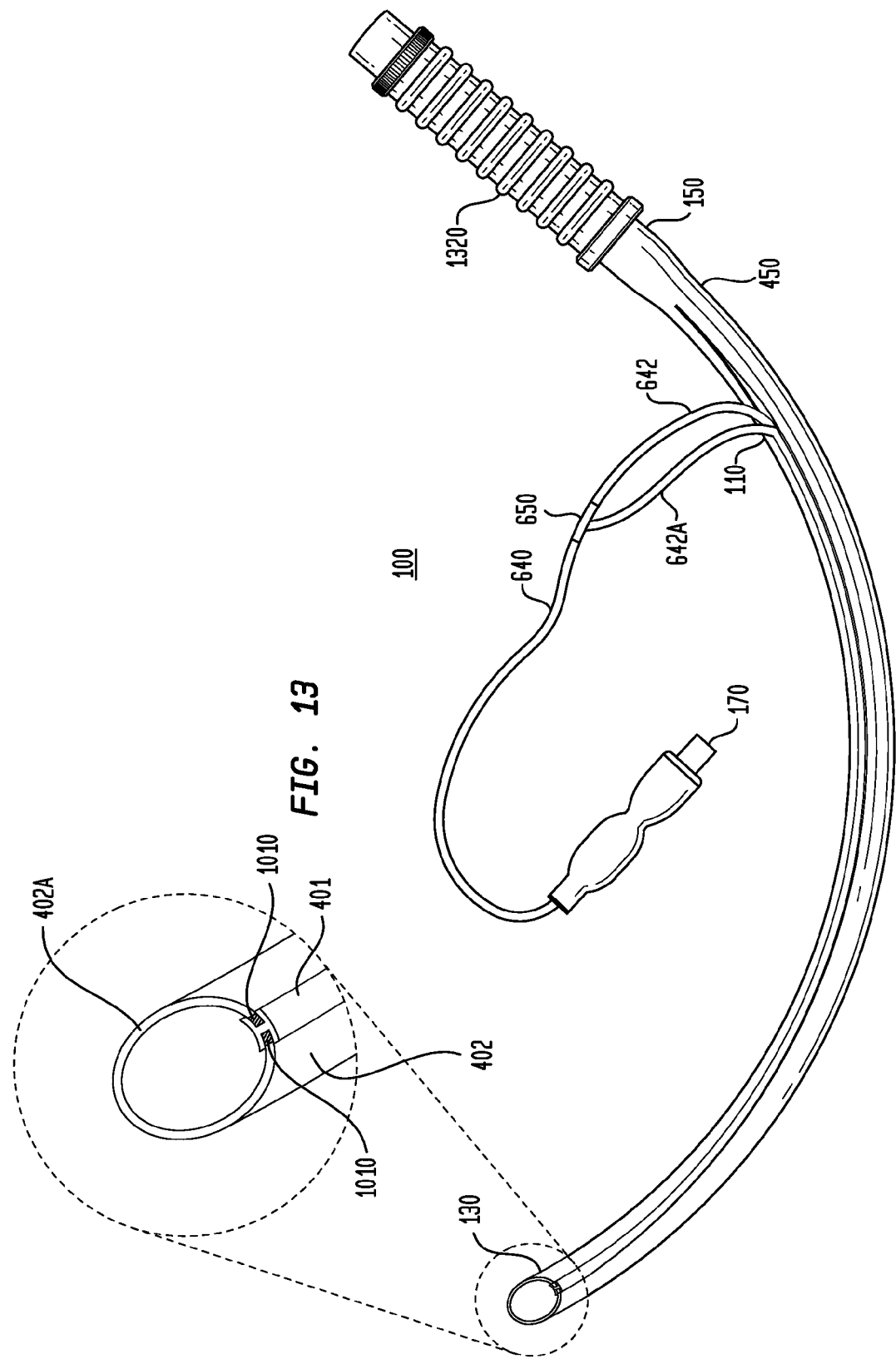
FIG. 13 illustrates a perspective view of one aspect of the inter vivos tube in accordance with the principles of the invention.

FIG. 13 illustrates an exemplary embodiment of an inter vivos tube 400 in accordance with the principles of the invention.

In this illustrative embodiment, distal end 130 is shown in an expanded view, wherein plugs 1010 are incorporated into the distal end to retain balloons 470, 470A (not shown) as previously disclosed. In addition, accordion type connector 1320 is shown attached to proximal end 150 to which tube 330 (see FIG. 11) may be subsequently attached.

Figure 14:
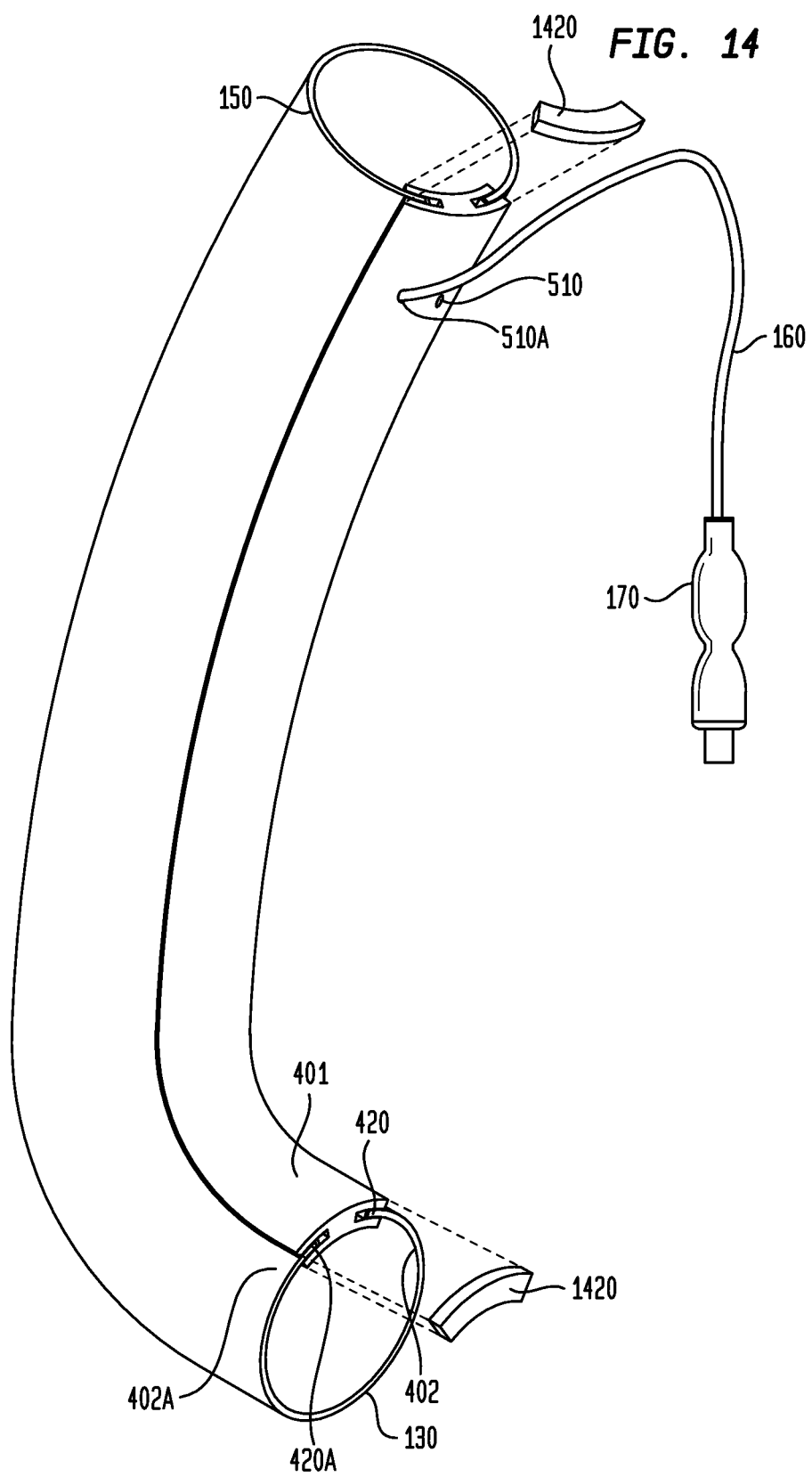
FIG. 14 illustrates a perspective view of another aspect of the inter vivos tube in accordance with the principles of the invention.

FIG. 14 illustrates an exemplary embodiment of an inter vivos tube 400 in accordance with the principles of the invention.

In this illustrative embodiment, distal end 130 and proximal end 150 are shown sealed by flaps 1420 to retain balloons 470, 470A (not shown) as previously discussed.

A method of manufacturing the inter vivos tube 400 may, for example, represent the formation of H-shaped member 401 by an extrusion process to form rib 431, and inner and outer arched segments 403A, 403, respectively. Balloons 470, 470A may be inserted through ingress ports 510, 510A. For example, balloons 470, 470A may be threaded into corresponding cavities 470, 470A through a needle insertion. After balloons 470, 470A are threaded into cavities 438, 439, respectively, air tubes 642, 642A, which are attached to a proximal end of corresponding balloons 470, 470A, exit through ingress ports 510, 510A, respectively.

Although the invention has been described with regard to preferred embodiments of the invention claimed, it is expressly intended that all combinations of those elements that perform substantially the same function in substantially the same way to achieve the same results are within the scope of the invention. Substitutions of elements from one described embodiment to another are also fully intended and contemplated.

The terms "a" or "an" as used herein are to describe elements and components of the invention. This is done merely for convenience and to give a general sense of the invention. The description herein should be read to include one or at least one and the singular also includes the plural unless indicated to the contrary.

The term "comprises", "comprising", "includes", "including", "as", "having", or any other variation thereof, are intended to cover non-exclusive inclusions. For example, a process, method, article or apparatus that comprises a list of elements is not necessarily limited to only those elements but may include other elements not expressly listed or inherent to such process, method, article, or apparatus. In addition, unless expressly stated to the contrary, the term "or" refers to an inclusive "or" and not to an exclusive "or". For example, a condition A or B is satisfied by any one of the following: A is true (or present) and B is false (or not present); A is false (or not present) and B is true (or present); and both A and B are true (or present).

What is claimed is:

1. An expandable inter vivos tube comprising:
   a flexible member extending longitudinally substantially along an edge of said inter vivos tube, said flexible member comprising:
   an outer circumference member;
   an inner circumference member; and
   a rib element connecting said outer circumference member and said inner circumference member at substantially a midpoint of said outer circumference member and said inner circumference member, said outer circumference member, said inner circumference member and said rib member forming a first cavity and a second cavity, respectively,
   a balloon, extending longitudinally in each of said first cavity and said second cavity, said balloon including a tube extending through a corresponding injection port in said flexible member; and
   a flexible longitudinal tube member having a first free end and a second free end, said first free end and second free end slidably engaging said balloon member in a corresponding one of said first cavity and said second cavity.

2. The inter vivos tube of claim 1, further comprising:
   sealing means associated with each of a distal end of said flexible member and a proximal end of said flexible member.

3. The inter vivos tube of claim 1, wherein said first free end and said second free end are tapered.

4. The inter vivos tube of claim 1, wherein said balloon comprising a material having an expansion capability greater at a distal end of said balloon than at a proximal end of said balloon.

5. The inter vivos tube of claim 1, wherein said rib has a greater width at a distal end of said flexible member than at a proximal end of said flexible member.

6. The inter vivos tube of claim 1, wherein said injection ports are at substantially one of: a distal end and a proximal end of said flexible member.

7. The inter vivos tube of claim 6, wherein said injection ports are in one of: said outer circumference member and said inner circumference member.

8. The inter vivos tube of claim 1, further comprising;
   a plurality of serrations on each of said first free end and said second free end; and
   a retaining pin positioned on at least a portion of an edge of one of: the lower circumference member and the outer circumference member, said retaining pin positioned opposite said plurality of serrations.

9. The inter vivos tube of claim 1, further comprising an optical channel in said flexible member.

10. The inter vivos tube of claim 1, wherein said inner circumference member is thinner than said outer circumference member.

11. An inter vivos tube comprising:
an H-shaped member extending longitudinally along said inter vivos tube, said H-shaped member comprising:
an upper arched segment,
a lower arched segment, and
a rib joining said upper arched segment and said lower arched segment forming a first cavity and a second cavity between said lower arched segment and said upper arched segment;
a first inflatable balloon in said first cavity, said first inflatable balloon having integrated therein a first hollow tube connector, where a second end of said first hollow tube connector extends through one of: said upper arched segment and said lower arched segment,
a second inflatable balloon in said second cavity, said second inflatable balloon having integrated thereon a second hollow tube connector, wherein a second end of said second hollow tube connector extends through one of: said upper arched segment and said lower arched segment;
and a tube member having a first free end and a second free end, said first free end slidably engaging said first cavity and said second free end slidably engaging said second cavity.

12. The inter vivos tube of claim 11, wherein said first inflatable balloon is attached to said first free end and said second inflatable balloon is attached to said second free end.

13. The inter vivos tube of claim 11, further comprising:
sealing means at each of a distal end and a proximal end of said first cavity and said second cavity.

14. The inter vivos tube of claim 11, said H-shaped member comprising:
a first ingress port and a second ingress port positioned on opposite sides of said rib, said second end of said first hollow connector passing through said first ingress port and said second end of said second hollow connector passing through said second ingress port.

15. The inter vivos tube of claim 11, wherein said first ingress port and said second ingress port are positioned at substantially a proximal end of said upper arched segment.

16. The inter vivos tube of claim 11, wherein said rib is wider at a distal end of said H-shaped member then at a proximal end of said H-shaped member.

17. The inter vivos tube of claim 11, wherein said lower arched segment is thinner than said upper arched segment.

18. The inter vivos tube of claim 11, further comprising:
a Y-connector attached to said second end of each of said first hollow tube connector and said second hollow tube connector.

19. The inter vivos tube of claim 11, wherein said first flexible balloon and said second flexible balloon are each composed of a material having a greater flexibility at one of: a distal end and a proximal end than at the other of the distal end and the proximal end.

20. The inter vivos tube of claim 11, further comprising:
an connector attached to said proximal end of said inter vivos tube.

* * * * *